United States Patent
Zeng et al.

(10) Patent No.: US 12,102,393 B2
(45) Date of Patent: Oct. 1, 2024

(54) SURGICAL ROBOTIC ARM CONTROL SYSTEM AND CONTROL METHOD THEREOF

(71) Applicant: Metal Industries Research & Development Centre, Kaohsiung (TW)

(72) Inventors: Jian Jia Zeng, Kaohsiung (TW); Bo-Wei Pan, Kaohsiung (TW); Sheng-Hong Yang, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 528 days.

(21) Appl. No.: 17/527,174

(22) Filed: Nov. 16, 2021

(65) Prior Publication Data
US 2023/0149095 A1    May 18, 2023

(51) Int. Cl.
*A61B 34/20*    (2016.01)
*A61B 34/32*    (2016.01)

(52) U.S. Cl.
CPC .............. *A61B 34/20* (2016.02); *A61B 34/32* (2016.02); *A61B 2034/2057* (2016.02); *A61B 2034/2065* (2016.02); *A61B 2034/2074* (2016.02)

(58) Field of Classification Search
CPC . A61B 34/20; A61B 34/32; A61B 2034/2057; A61B 2034/2065; A61B 2034/2074; A61B 34/30
See application file for complete search history.

(56) References Cited

U.S. PATENT DOCUMENTS

| | | |
|---|---|---|
| 2017/0182660 A1 | 6/2017 | Pipitone |
| 2018/0354130 A1 | 12/2018 | Preisinger et al. |
| 2019/0099222 A1 | 4/2019 | Nahum et al. |
| 2019/0143517 A1* | 5/2019 | Yang ............... G06N 5/046 700/245 |
| 2019/0224841 A1 | 7/2019 | Ly et al. |
| 2019/0350661 A1 | 11/2019 | Fukushima et al. |

(Continued)

FOREIGN PATENT DOCUMENTS

| | | |
|---|---|---|
| CN | 101763040 | 6/2010 |
| CN | 106607920 | 5/2017 |

OTHER PUBLICATIONS

"Office Action of Taiwan Counterpart Application", issued on Mar. 29, 2023, p. 1-p. 4.

*Primary Examiner* — Jason Holloway
*Assistant Examiner* — Madison B Emmett
(74) *Attorney, Agent, or Firm* — JCIPRNET

(57) ABSTRACT

A surgical robotic arm control system and a control method thereof are provided. The surgical robotic arm control system includes a surgical robotic arm, an image capturing unit, and a processor. The surgical robotic arm has multiple joint axes. The image capturing unit obtains a first image. The processor executes a spatial environment recognition module to generate a first environment information image, a first direction information image, and a first depth information image according to the first image. The processor executes a spatial environment image processing module to calculate path information according to the first environment information image, the first direction information image, and the first depth information image. The processor executes a robotic arm motion feedback module to operate the surgical robotic arm to move according to the path information.

20 Claims, 7 Drawing Sheets

(56) References Cited

U.S. PATENT DOCUMENTS

| | | | |
|---|---|---|---|
| 2020/0094405 A1 | 3/2020 | Davidson et al. | |
| 2020/0345451 A1* | 11/2020 | Peine | A61B 34/35 |
| 2020/0380687 A1* | 12/2020 | Avital | A61B 8/5207 |
| 2020/0410666 A1* | 12/2020 | Wagner | G06N 3/08 |
| 2021/0378748 A1* | 12/2021 | Leist | A61B 34/30 |
| 2022/0031395 A1* | 2/2022 | Bono | A61B 8/5207 |
| 2022/0104884 A1* | 4/2022 | Leiderman | A61B 1/000095 |
| 2022/0160445 A1* | 5/2022 | Meglan | B25J 9/1676 |
| 2023/0125022 A1* | 4/2023 | Li | B25J 9/1656 700/245 |
| 2024/0050172 A1* | 2/2024 | Wu | A61B 34/30 |

\* cited by examiner

SURGICAL ROBOTIC ARM CONTROL SYSTEM AND CONTROL METHOD THEREOF

BACKGROUND

Technical Field

The disclosure relates to an automatic control technology. Particularly, the disclosure relates to a surgical robotic arm control system and a control method thereof.

Description of Related Art

With the development of medical equipment, relevant automatically controllable medical equipment, which helps assist medical personnel in surgical efficiency, is currently one of the important development directions in the related field. In particular, during a surgery, a surgical robotic arm for assisting or cooperating with the medical personnel (surgery performer) in related operations is relatively important. However, in the existing surgical robotic arm design, for the surgical robotic arm to realize automatic control function, it requires the surgical robotic arm to be provided with a plurality of sensors, and requires a user to perform complicated and trivial manual correction operations during each operation, for the surgical robotic arm to avoid obstacles in the path during movement, achieving accurate automatic movement and automatic operation results.

SUMMARY

The disclosure provides a surgical robotic arm control system and a control method thereof, in which a surgical robotic arm can be effectively controlled to move automatically.

A surgical robotic arm control system of the disclosure includes a surgical robotic arm, an image capturing unit, and a processor. The surgical robotic arm has a plurality of joint axes. The image capturing unit obtains a first image. The first image includes a robotic arm distal end image of the surgical robotic arm. The processor is coupled to the surgical robotic arm and the image capturing unit. The processor executes a spatial environment recognition module to generate a first environment information image, a first direction information image, and a first depth information image according to the first image. The processor executes a spatial environment image processing module to calculate path information according to the first environment information image, the first direction information image, and the first depth information image. The processor executes a robotic arm motion feedback module to operate the surgical robotic arm to move according to the path information.

A surgical robotic arm control method of the disclosure includes the following. A first image is obtained by an image capturing unit. The first image comprises a robotic arm distal end image of a surgical robotic arm. A spatial environment recognition module is executed by a processor to generate a first environment information image, a first direction information image, and a first depth information image according to the first image. A spatial environment image processing module is executed by the processor to calculate path information according to the first environment information image, the first direction information image, and the first depth information image. A robotic arm motion feedback module is executed by the processor to operate the surgical robotic arm to move according to the path information.

Based on the foregoing, the surgical robotic arm control system and the control method thereof of the disclosure, the surgical robotic arm can be automatically controlled to move through computer vision image technology, and can automatically avoid obstacles in the current environment.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
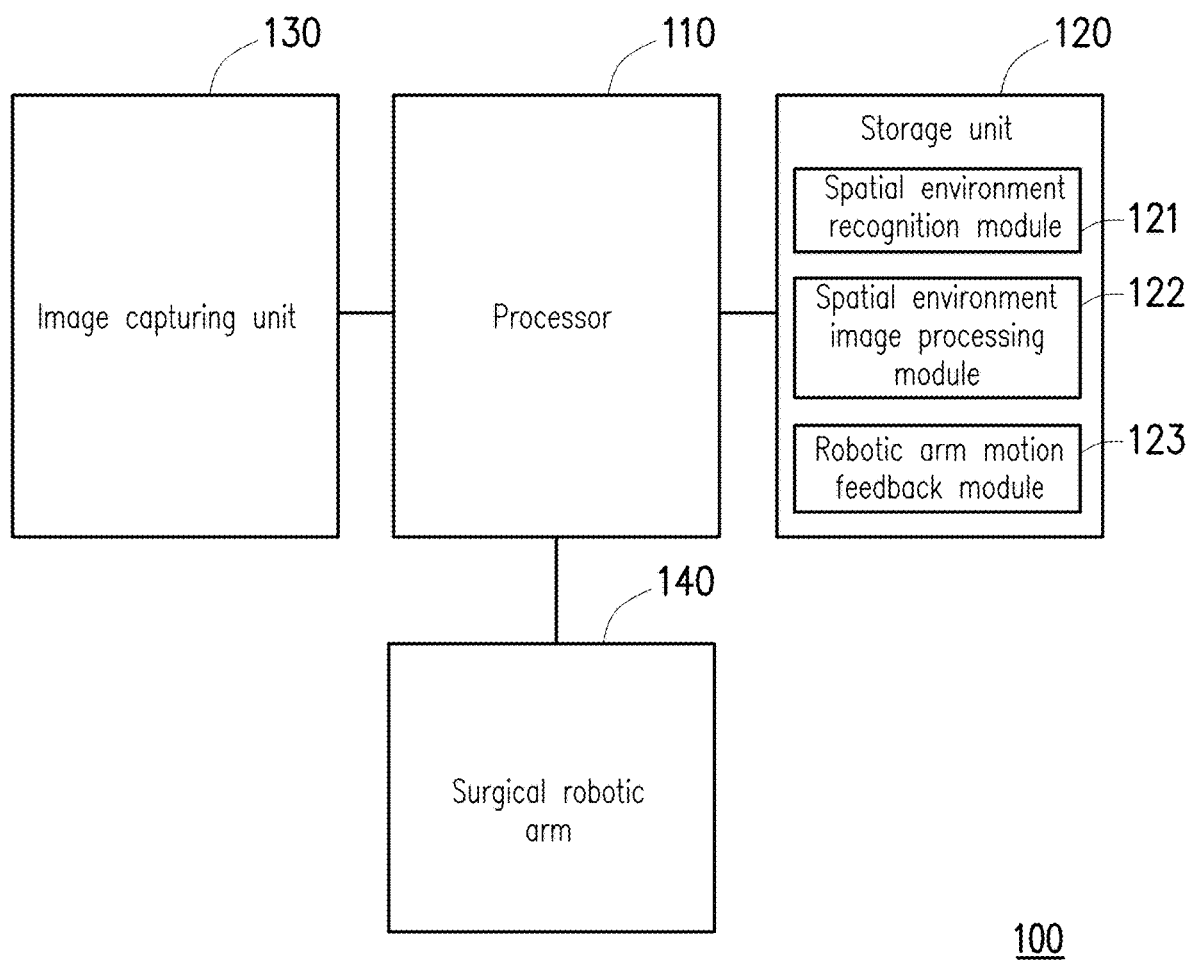
FIG. 1 is a schematic circuit block diagram of a surgical robotic arm control system according to an embodiment of the disclosure.

To make the content of the disclosure more comprehensible, embodiments are particularly provided below to serve as examples according to which the disclosure can reliably be implemented. In addition, wherever possible, elements/members/steps with the same reference numerals in the drawings and the embodiments denote the same or similar parts.

FIG. 1 is a schematic circuit block diagram of a surgical robotic arm control system according to an embodiment of the disclosure. With reference to FIG. 1, a surgical robotic arm control system 100 includes a processor 110, a storage unit 120, an image capturing unit 130, and a surgical robotic arm 140. The storage unit 120 stores a spatial environment recognition module 121, a spatial environment image processing module 122, and a robotic arm motion feedback module 123. The processor 110 is coupled to the storage unit 120, the image capturing unit 130, and the surgical robotic arm 140. The surgical robotic arm 140 has a plurality of joint axes. In this embodiment, the image capturing unit 130 may obtain image data and provide the image data to the processor 110. The processor 110 may access the storage unit 120 to execute the spatial environment recognition module 121, the spatial environment image processing module 122, and the robotic arm motion feedback module 123. In this embodiment, the processor 110 may input relevant image data to the spatial environment recognition module 121 and the spatial environment image processing module 122 to generate path information, and the processor 110 may operate the surgical robotic arm 140 to move according to the path information.

In this embodiment, the surgical robotic arm control system 100 may be integrated with the mechanism of a surgical platform. The image capturing unit 130 may be disposed on the upper side of the surgical platform (directly above the surgical platform or above the surgical platform with an offset by an angle) to photograph toward the surgical platform and the surgical robotic arm 140. In addition, the surgical robotic arm 140 may be disposed on a side of the surgical platform. In this embodiment, the surgical robotic arm control system 100 may control the surgical robotic arm 140 to move from one side of the surgical platform to the other end of the surgical platform, and the surgical robotic arm 140 and its robotic arm distal end can automatically avoid obstacles on the movement path. Therefore, the surgical personnel can quickly grasp the surgical robotic arm 140 to perform surgical assistance at the other end of the surgical platform.

In this embodiment, the processor 110 may be, for example, a central processing unit (CPU), or any other programmable general-purpose or special-purpose microprocessor, a digital signal processor (DSP), an image processing unit (IPU), a graphics processing unit (GPU), a programmable controller, an application specific integrated circuit (ASIC), a programmable logic device (PLD), other similar processing devices, or a combination of these devices.

In this embodiment, the storage unit 120 may be memory, for example, dynamic random access memory (DRAM), flash memory, or non-volatile random access memory (NVRAM), which is not limited by the disclosure. The storage unit 120 may store the spatial environment recognition module 121, the spatial environment image processing module 122, the robotic arm motion feedback module 123, and relevant algorithms of modules mentioned in the embodiments of the disclosure. In addition, the storage unit 120 may also store, for example, image data, robotic arm control commands, robotic arm control software, and computing software, among other related algorithms, programs, and data configured to realize the surgical robotic arm control of the disclosure. In this embodiment, the spatial environment recognition module 121 and the spatial environment image processing module 122 may be respectively neural network modules that realize corresponding functions.

In this embodiment, the surgical robotic arm 140 may be a robotic arm with six degree of freedom (6DOF), and the processor 110 may execute a machine learning module applying Markov decision process to control the surgical robotic arm 140. In this embodiment, the image capturing unit 130 may be, for example, a depth camera, and may be configured to photograph a surgical field to obtain a field image and its depth information. In an embodiment, the storage unit 120 may also store a panoramic environment field positioning module. The processor 110 may execute the panoramic environment field positioning module to perform a camera calibration computation, and the processor 110 may realize coordinate system matching between the image capturing unit 130 and the surgical robotic arm 140. In this embodiment, the image capturing unit 130 may obtain a positioning image and reference depth information in advance. The positioning image includes a positioning object. The processor 110 may analyze positioning coordinate information and the reference depth information of the positioning object in the positioning image through the panoramic environment field positioning module to match a camera coordinate system of the image capturing unit 130 (the depth camera) and a robotic arm coordinate system of the surgical robotic arm 140.

Specifically, a user may, for example, take a positioning board having a pattern of a chessboard image as the positioning object and place it on the surgical platform, so that the image capturing unit 130 may capture a plurality of positioning images. The positioning images may each include the pattern of the chessboard image. The number of positioning images may be 5, for example. Then, the processor 110 may execute the panoramic environment field positioning module to analyze the positioning coordinate information (a plurality of spatial coordinates) and the reference depth information of the respective positioning objects in the positioning images through the panoramic environment field positioning module, to match the camera coordinate system (a spatial coordinate system) of the image capturing unit 130 and the robotic arm coordinate system (a spatial coordinate system) of the surgical robotic arm 140. The processor 110 may match the camera coordinate system of the image capturing unit 130 and the robotic arm coordinate system of the surgical robotic arm 140 according to fixed position relationships, the positioning coordinate information, and the reference depth information.

Figure 2:
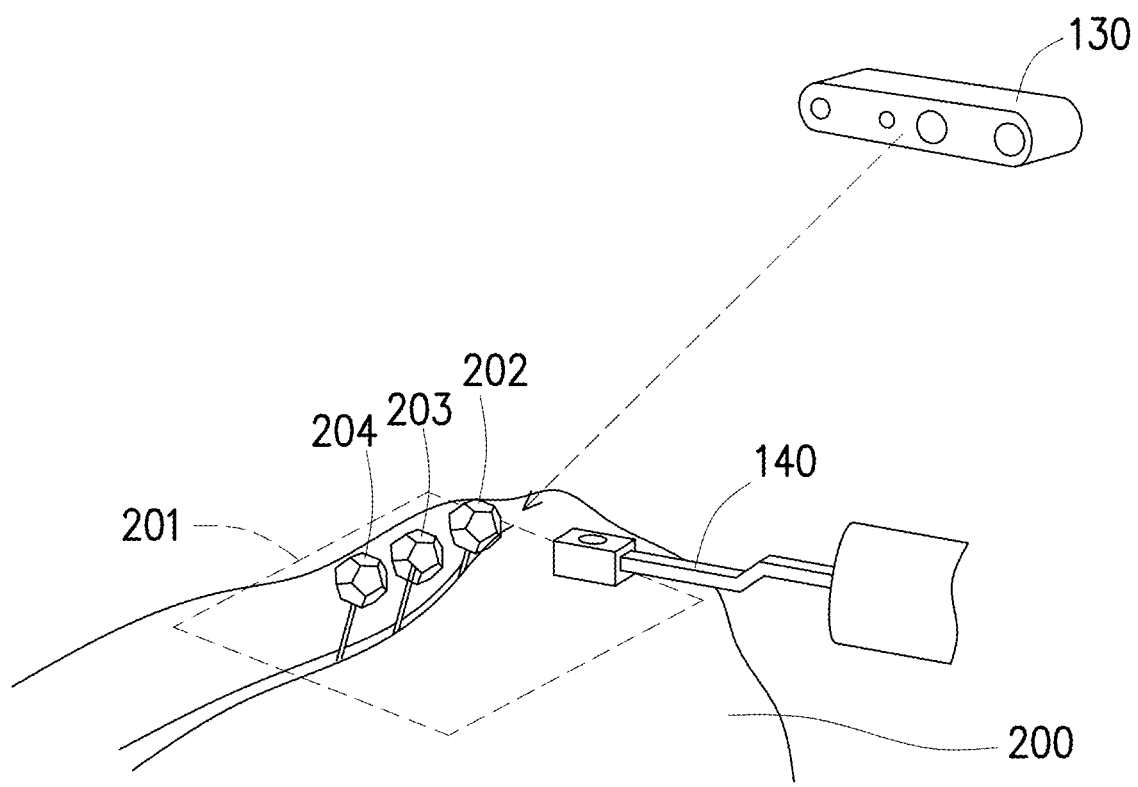
FIG. 2 is a schematic diagram of operation of a surgical robotic arm control system according to an embodiment of the disclosure.
Figure 3:
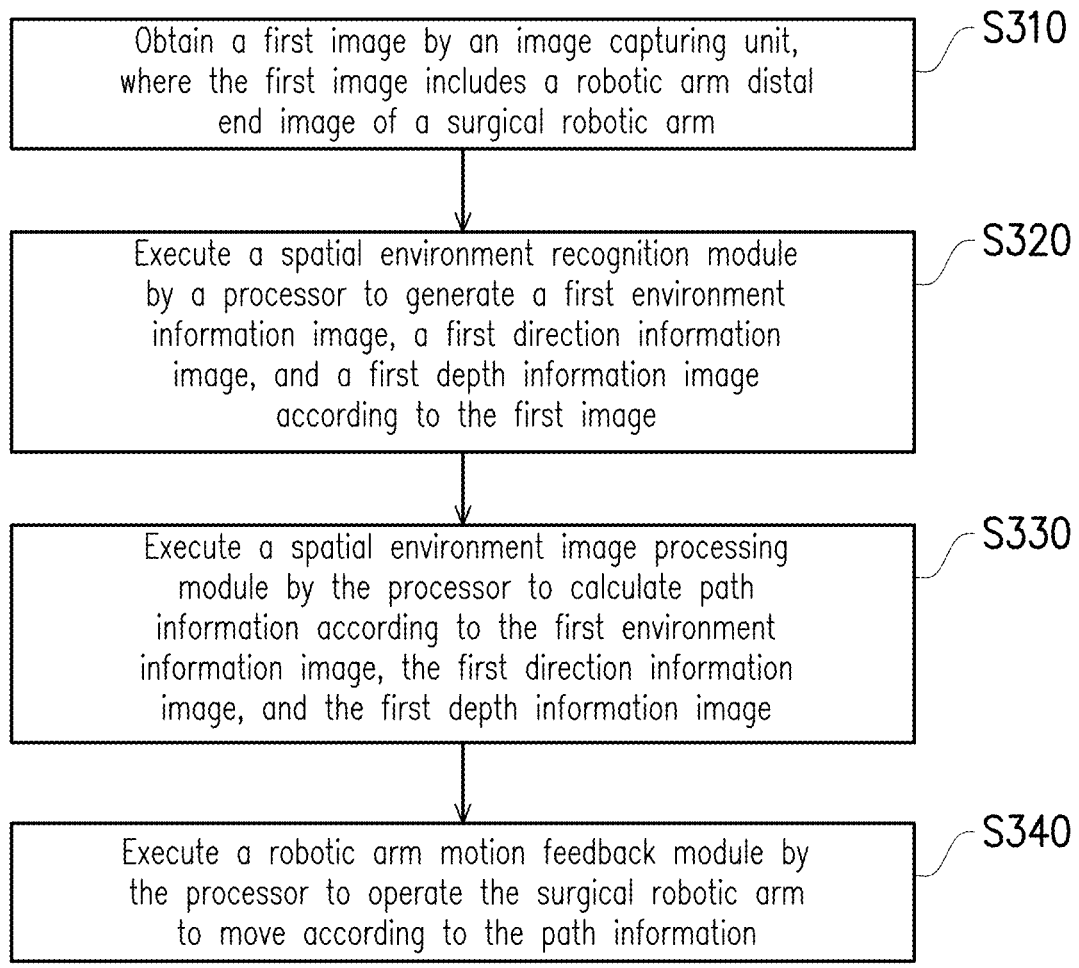
FIG. 3 is a flowchart of a surgical robotic arm control method according to an embodiment of the disclosure.
Figure 4:
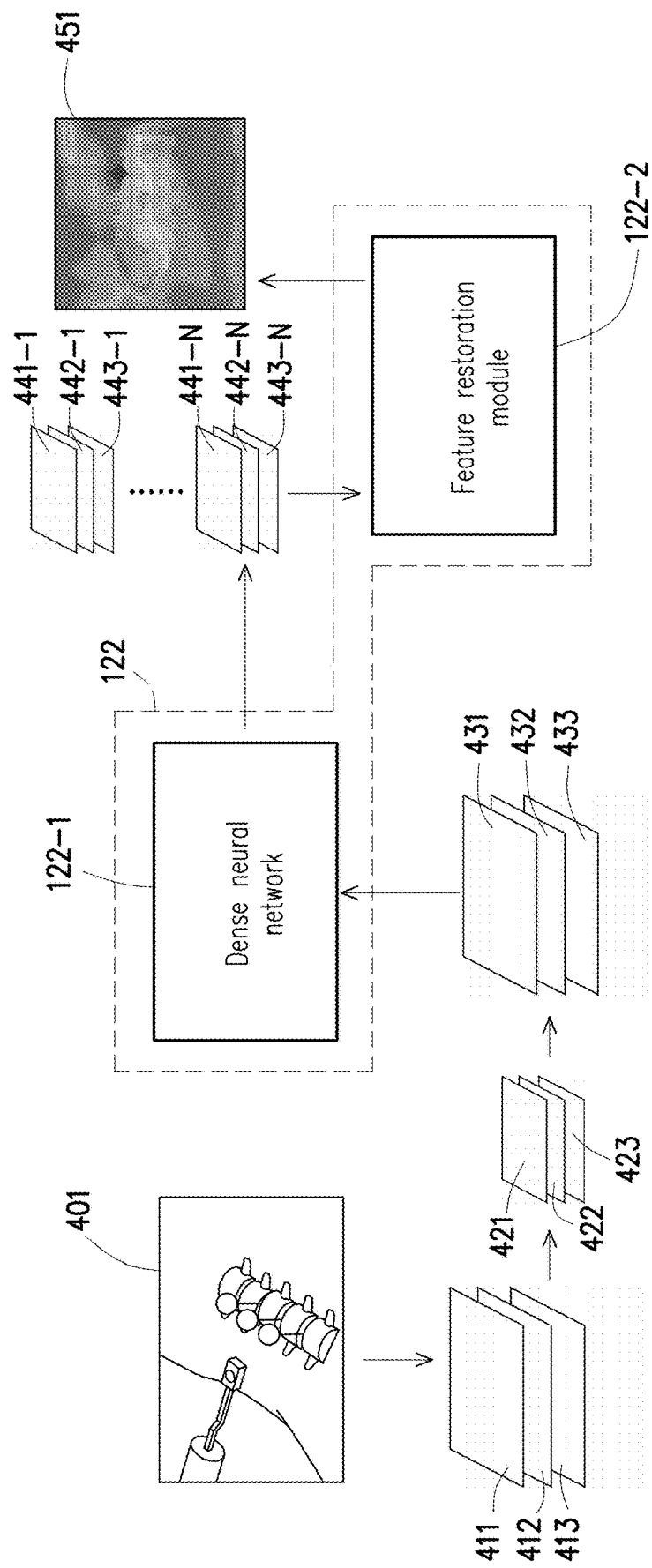
FIG. 4 is a schematic diagram of image processing and image analysis according to an embodiment of the disclosure.

FIG. 2 is a schematic diagram of operation of a surgical robotic arm control system according to an embodiment of the disclosure. FIG. 3 is a flowchart of a surgical robotic arm control method according to an embodiment of the disclosure. FIG. 4 is a schematic diagram of image processing and image analysis according to an embodiment of the disclosure. With reference to FIG. 1 to FIG. 4, the image capturing unit 130 may, for example, photograph toward a surgical platform. A surgical target 200, for example, may be placed on the surgical platform. In this embodiment, the surgical robotic arm 140 may be located on the side of the surgical target 200 as shown in FIG. 2, and the processor 110 may control the surgical robotic arm 140 to move to another side in a surgical region 201 of the surgical target 200. In addition, obstacles on the movement path in the surgical region 201 can be automatically avoided, where the obstacles may include, for example, surgical instruments 202 to 204 placed on the surgical target 200.

In this embodiment, the surgical robotic arm control system 100 may perform steps S310 to S340 below. In step S310, the surgical robotic arm control system 100 may obtain a first image 401 (a current frame) by the image capturing unit 130. The first image 401 includes a robotic arm distal end image of the surgical robotic arm 140. In this embodiment, the storage unit 120 may also store a target region confirmation module, and the surgical robotic arm control system 100 may also include an input unit. The input unit may be, for example, a mouse, a touch screen, a user interface, a system setting module, or the like, and may provide a target coordinate to the processor 110. In this regard, the processor 110 may execute the target region confirmation module to define a target region in the first image 401 according to the target coordinate. In this regard, the target region is a spatial region (a virtual cube), and may be, for example, on another side of a surgical target in the first image 401.

In step S320, the surgical robotic arm control system 100 may execute the spatial environment recognition module 121 by the processor 110 to generate a first environment information image 411, a first direction information image 412, and a first depth information image 413 according to the first image 401. In step S330, the surgical robotic arm control system 100 may execute the spatial environment image processing module 122 by the processor 110 to calculate path information according to the first environment information image 411, the first direction information image 412, and the first depth information image 413. In this embodiment, according to a robotic arm distal end region of the surgical robotic arm 140, the spatial environment image processing module 122 may extract a second environment information image 421, a second depth information image 422, and a second direction information image 423 (where only the robotic arm distal end image of the image is extracted for subsequent calculation and analysis) respectively from the first environment information image 411, and the first depth information image 413, and the first direction information image 412. In this regard, since the second environment information image 421, the second depth information image 422, and the second direction information image 423 are respectively a part of the first environment information image 411, a part of the first depth information image 413, and a part of the first direction information image 412, the surgical robotic arm control system 100 in the disclosure may perform rapid image calculation and analysis for key regions of the image of each frame, and the computing resources can be effectively saved and the calculation can be performed quickly to move the surgical robotic arm 140 to the target coordinate.

For example, the first environment information image 411, the first direction information image 412, and the first depth information image 413 may each have an image resolution of 224×224 pixels, and the second environment information image 421, the second depth information image 422, and the second direction information image 423 may each have an image resolution of 54×54 pixels. Before the spatial environment image processing module 122 inputs the second environment information image 421, the second depth information image 422, and the second direction information image 423 to a fully convolutional network model 122, the spatial environment image processing module 122 may first perform image enlargement on each of the second environment information image 421, the second depth information image 422, and the second direction information image 423. The image magnification may be performed through, for example, a bilinear interpolation. An enlarged second environment information image 431, an enlarged second depth information image 432, and an enlarged second direction information image 433 may each have an image resolution of 224×224 pixels. Then, the spatial environment image processing module 122 may input the enlarged second environment information image 431, the enlarged second depth information image 432, and the enlarged second direction information image 433 to the fully convolutional network model 122 for the fully convolutional network model 122 to output a feature image 451.

The fully convolutional network model 122 may include a dense neural network 122-1 (the upper half of the calculation model) and a feature restoration module 122-2 (the lower half of the calculation model). The dense neural network 122-1 may first generate a plurality of feature value information 441-1 to 441-N, 442-1 to 442-N, 443-1 to 443-N of training results. The feature value information 441-1 to 441-N may be the training results of the enlarged second environment information image 431. The feature value information 442-1 to 442-N may be the training results of the enlarged second depth information image 432. The feature value information 443-1 to 443-N may be the training results of the enlarged second direction information image 433. The fully convolutional network model 122 may then input the feature value information 441-1 to 441-N, 442-1 to 442-N, 443-1 to 443-N to the feature restoration module 122-2 for the feature restoration module 122-2 to reorganize the feature value information 441-1 to 441-N, 442-1 to 442-N, 443-1 to 443-N to output the feature image 451. In this embodiment, the spatial environment image processing module 122 may analyze the feature image 451 to calculate the path information. The feature image 451 may, for example, have weight distribution information (movable weight or obstacle weight) corresponding to the position of each point in the space or the movement plane. In addition, the processor 110 may calculate, for example, information or parameters such as the movable direction and the movable distance of the surgical robotic arm 140 in the current frame according to the feature image 451.

In step S340, the surgical robotic arm control system 100 may execute the robotic arm motion feedback module 123 by the processor 110 to operate the surgical robotic arm 140 to move to the target region according to the path information. In this embodiment, the image capturing unit 130 may successively obtain a plurality of first images of a plurality of frames for the processor 110 to iteratively execute the spatial environment recognition module 121, the spatial environment image processing module 122, and the robotic arm motion feedback module 123 according to the first images to operate the surgical robotic arm 140 a plurality of times to move until the processor 110 determines that the robotic arm distal end of the surgical robotic arm 140 reaches the target coordinate. In this regard, when the processor 110 determines that the robotic arm distal end region of the surgical robotic arm 140 overlaps the target region (when the two virtual cubes are overlaid), the processor 110 may determine that the robotic arm distal end of the surgical robotic arm 140 reaches the target coordinate. The robotic arm distal end region may be a cubic region extending outward based on the center point of the spatial position of the robotic arm distal end as its center (where the center point of the region is the center point of the robotic arm distal end) simulated by the processor 110. Therefore, the surgical robotic arm 140 can automatically avoid the surgical instruments 202 to 204 on the movement path to automatically move to the other side of the surgical target 200.

Figure 5:
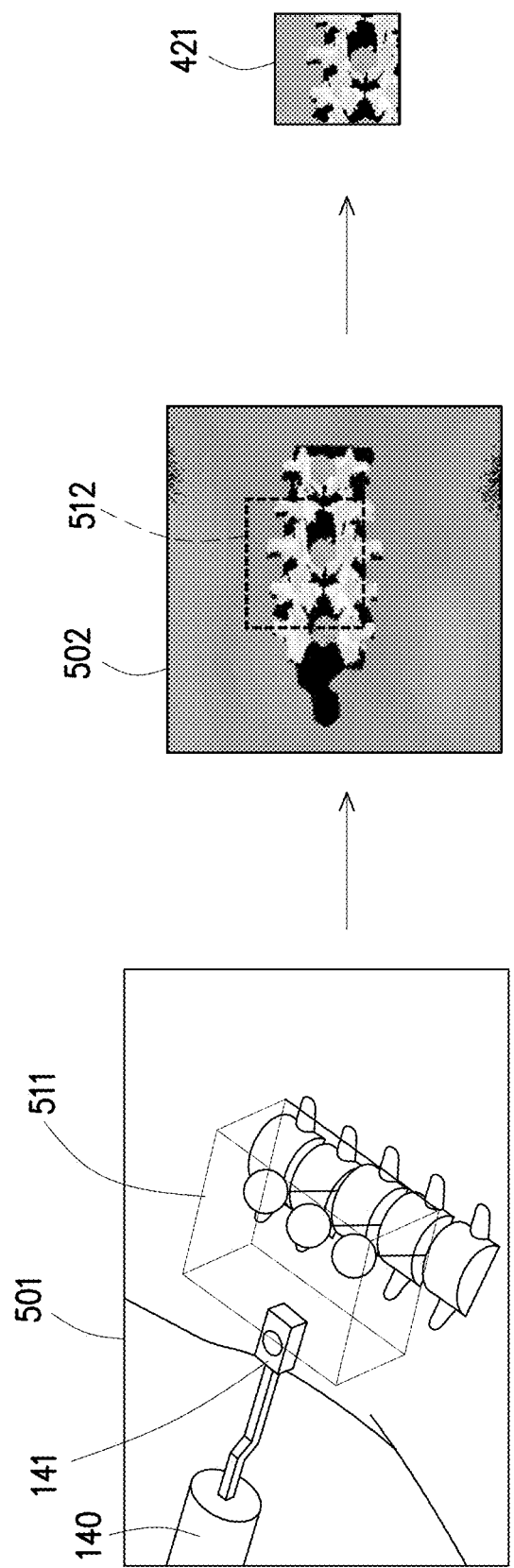
FIG. 5 is a schematic diagram of generating a second environment information image according to an embodiment of the disclosure.
Figure 6:
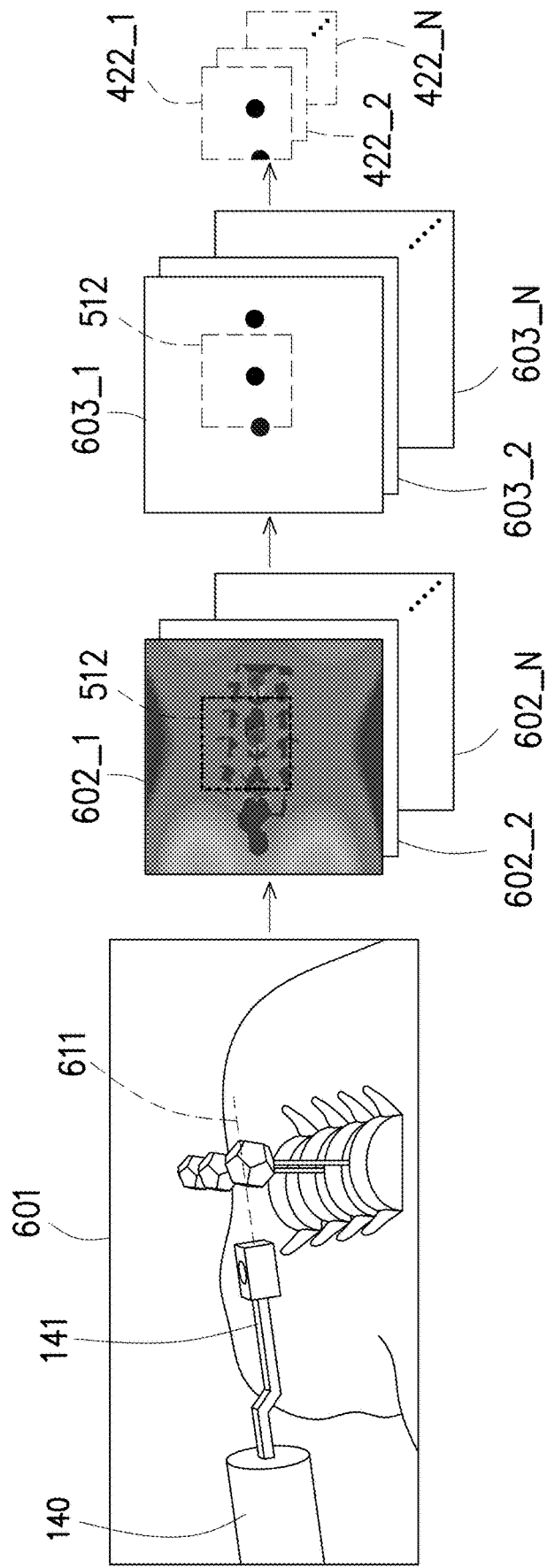
FIG. 6 is a schematic diagram of generating a second depth information image according to an embodiment of the disclosure.
Figure 7:
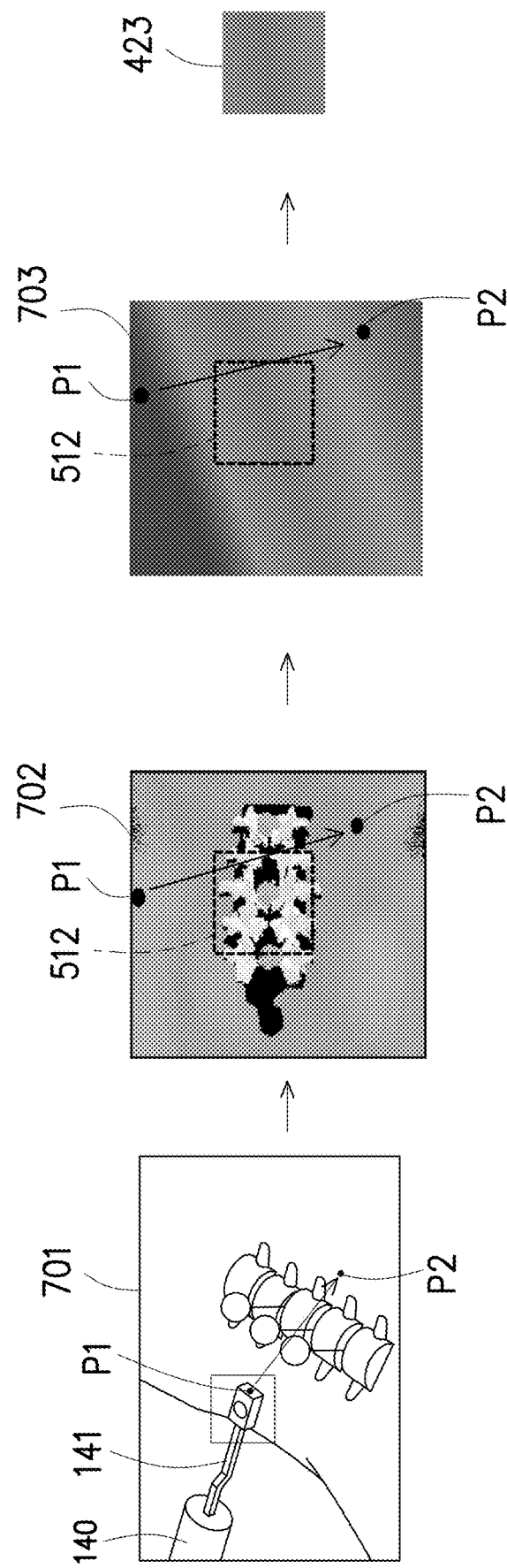
FIG. 7 is a schematic diagram of generating a second direction information image according to an embodiment of the disclosure.

The following embodiments of FIG. 5 to FIG. 7 will respectively describe in detail the generation of the second environment information image 421, the second depth information image 422, and the second direction information image 423.

FIG. 5 is a schematic diagram of generating a second environment information image according to an embodiment of the disclosure. With reference to FIG. 1 and FIG. 5, the image capturing unit 130 may, for example, photograph a surgical field 501 as shown in FIG. 5 to obtain a first environment information image 502 (i.e., the first image). The processor 110 may define a position of a robotic arm distal end corresponding to a surgical robotic arm in the first environment information image 502 to determine a range (a predetermined analysis range) of a robotic arm distal end region 511. In this regard, a horizontal range of the robotic arm distal end region 511 may correspond to a range 512 in the first environment information image 502. Then, the processor 110 may crop the first environment information image 502 according to the range 512 to generate the second environment information image 421 (an RGB image).

FIG. 6 is a schematic diagram of generating a second depth information image according to an embodiment of the disclosure. With reference to FIG. 1 and FIG. 6, the image capturing unit 130 may, for example, photograph a surgical field 601 as shown in FIG. 6 to obtain a first depth information image with depth information (i.e., the first image with depth information). The processor 110 may define a position of a robotic arm distal end corresponding to a surgical robotic arm in the first depth information image to determine a reference plane based on an extension axis 611 of the robotic arm distal end 141. The first depth information image may include a plurality of first depth planar images 602_1 to 602_N corresponding to different depths, where N is a positive integer. The different depths may refer to, for example, the reference plane and 5 planes both above and below, and parallel to, the reference plane at a vertical depth (e.g., −5, −4, −3, −2, −1, 0, 1, 2, 3, 4, 5). Nonetheless, the sampling number of the depth planar images is not limited by the disclosure. In this regard, a horizontal range of a robotic arm distal end region (similar to the robotic arm distal end region 511 of FIG. 5) of the robotic arm distal end 141 may correspond to the range 512 at the same position in the first depth planar images 6021 to 602_N. Then, the processor 110 may convert the first depth planar images 602_1 to 602_N into a plurality of binarized images 603_1 to 603_N (where the presence of obstacles is represented by a value "0" (pure black), while the absence of obstacles is represented by a value "1" (pure white), for example). In addition, the processor 110 may obtain a plurality of second depth planar images 422_1 to 422_N corresponding to different depths in a second depth information image from the binarized images 603_1 to 603_N according to the robotic arm distal end region of the surgical robotic arm 140. In this regard, the surgical robotic arm control system 100 may obtain obstacle distribution information (e.g., distribution information of other surgical instruments) on different depth planes according to the second depth planar images 422_1 to 422_N to effectively calculate the movement path where the surgical robotic arm 140 does not collide with obstacles.

FIG. 7 is a schematic diagram of generating a second direction information image according to an embodiment of the disclosure. With reference to FIG. 1 and FIG. 7, the image capturing unit 130 may, for example, photograph a surgical field 701 as shown in FIG. 7 to obtain a first environment information image 702 (i.e., the first image). The processor 110 may define a robotic arm distal end corresponding to a surgical robotic arm in the first environment information image 702 to determine a robotic arm distal end point P1 taking the endpoint of the robotic arm distal end as a current frame. The processor 110 may define the robotic arm distal end of the surgical robotic arm in the first environment information image 702 to determine a range (a predetermined analysis range) of a robotic arm distal end region. In addition, the processor 110 may obtain a target coordinate according to a target selection signal (in which, for example, the user selects the target position) provided by an input unit to determine a target point P2. Along a path from the robotic arm distal end point P1 to the target point P2 in the first environment information image 702 and depending on different distances to the target point P2, the processor 110 may determine radioactive gradient color parameters to generate a first direction information image 703. It is worth noting that a color changing direction of the first direction information image 703 is parallel to a direction from a robotic arm distal end coordinate of the robotic arm distal end point P1 to the target coordinate of the target point P2 in the first direction information image 703. The processor 110 may crop the first direction information image 703 according to the range 512 to generate the second direction information image 423.

In summary of the foregoing, in the surgical robotic arm control system and control method thereof of the disclosure, the automatic control of the surgical robotic arm to move and to approach the target object by utilizing computer vision image technology can be achieved through the image capturing unit, and through concentration of computing resources on computing and analyzing key regions in the sensed image provided by the image capturing unit, quick and accurate control of the surgical robotic arm can be achieved. Therefore, in the surgical robotic arm control system and control method thereof of the disclosure, the surgical robotic arm can be effectively caused to automatically move to, for example a position adjacent to the hand of the surgical personnel or the surgical target, so that the surgical personnel can quickly and efficiently use the surgical robotic arm to realize the surgical assistance.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A surgical robotic arm control system, comprising:
a surgical robotic arm, having a plurality of joint axes;
an image capturing unit, configured to obtain a first image, wherein the first image comprises a robotic arm distal end image of the surgical robotic arm; and
a processor, coupled to the surgical robotic arm and the image capturing unit,
wherein the processor executes a spatial environment recognition module to generate a first environment information image, a first direction information image, and a first depth information image according to the first image, and the processor executes a spatial environment image processing module to calculate path information according to the first environment information image, the first direction information image, and the first depth information image, and
wherein the processor executes a robotic arm motion feedback module to operate the surgical robotic arm to move according to the path information.

2. The surgical robotic arm control system as described in claim 1, wherein the image capturing unit is a depth camera, and the image capturing unit obtains a positioning image and reference depth information in advance, wherein the positioning image comprises a positioning object,
wherein the processor executes a panoramic environment field positioning module to analyze positioning coordinate information and the reference depth information of the positioning object in the positioning image through the panoramic environment field positioning module, to match a camera coordinate system of the depth camera with a robotic arm coordinate system of the surgical robotic arm.

3. The surgical robotic arm control system as described in claim 1, wherein the processor executes a target region confirmation module to define a target region in the first image according to a target coordinate, and the robotic arm motion feedback module operates the surgical robotic arm to move to the target region.

4. The surgical robotic arm control system as described in claim 3, wherein the spatial environment image processing module extracts a second environment information image, a second direction information image, and a second depth information image respectively from the first environment information image, the first direction information image, and the first depth information image according to a robotic arm distal end region of the surgical robotic arm, and inputs the second environment information image, the second direction information image, and the second depth information image to a fully convolutional network model, such that the fully convolutional network model outputs a feature image, and the processor generates the path information according to the feature image, and wherein the second environment information image, the second direction information image, and the second depth information image are respectively a part of the first environment information image, a part of the first direction information image, and a part of the first depth information image.

5. The surgical robotic arm control system as described in claim 4, wherein before the processor inputs the second environment information image, the second direction information image, and the second depth information image to the fully convolutional network model, the processor first performs image enlargement on each of the second environment information image, the second direction information image, and the second depth information image.

6. The surgical robotic arm control system as described in claim 4, wherein the first depth information image comprises a plurality of first depth planar images corresponding to different depths, the processor converts the first depth planar images into a plurality of binarized images, and obtains a plurality of second depth planar images corresponding to different depths in the second depth information image from the binarized images according to the robotic arm distal end region of the surgical robotic arm.

7. The surgical robotic arm control system as described in claim 4, wherein when the processor determines that the robotic arm distal end region of the surgical robotic arm overlaps the target region, the processor determines that a robotic arm distal end of the surgical robotic arm reaches the target coordinate.

8. The surgical robotic arm control system as described in claim 7, wherein the image capturing unit successively obtains a plurality of first images, such that the processor iteratively executes the spatial environment recognition module, the spatial environment image processing module, and the robotic arm motion feedback module according to the first images to operate the surgical robotic arm a plurality of times to move until the processor determines that the robotic arm distal end of the surgical robotic arm reaches the target coordinate.

9. The surgical robotic arm control system as described in claim 4, wherein a color changing direction of the second direction information image is parallel to a direction from a robotic arm distal end coordinate to the target coordinate in the second direction information image.

10. The surgical robotic arm control system as described in claim 3, further comprising:

an input unit, coupled to the processor and providing a target selection signal to the processor, such that the processor generates the target coordinate according to the target selection signal.

11. A surgical robotic arm control method, comprising:

obtaining a first image by an image capturing unit, wherein the first image comprises a robotic arm distal end image of a surgical robotic arm;

executing a spatial environment recognition module by a processor to generate a first environment information image, a first direction information image, and a first depth information image according to the first image;

executing a spatial environment image processing module by the processor to calculate path information according to the first environment information image, the first direction information image, and the first depth information image; and executing a robotic arm motion feedback module by the processor to operate the surgical robotic arm to move according to the path information.

12. The surgical robotic arm control method as described in claim 11, wherein the image capturing unit is a depth camera, and the image capturing unit obtains a positioning image and reference depth information in advance, wherein the positioning image comprises a positioning object, and the surgical robotic arm control method comprises:

executing a panoramic environment field positioning module by the processor to analyze positioning coordinate information and the reference depth information of the positioning object in the positioning image through the panoramic environment field positioning module, to match a camera coordinate system of the depth camera with a robotic arm coordinate system of the surgical robotic arm.

13. The surgical robotic arm control method as described in claim 11, further comprising:

executing a target region confirmation module by the processor to define a target region in the first image according to a target coordinate, and operating, by the robotic arm motion feedback module, the surgical robotic arm to move to the target region.

14. The surgical robotic arm control method as described in claim 13, wherein executing the spatial environment image processing module by the processor to calculate the path information according to the first environment information image, the first direction information image, and the first depth information image comprises:

by the spatial environment image processing module, extracting a second environment information image, a second direction information image, and a second depth information image respectively from the first environment information image, the first direction information image, and the first depth information image according to a robotic arm distal end region of the surgical robotic arm; and by the spatial environment image processing module, inputting the second environment information image, the second direction information image, and the second depth information image to a fully convolutional network model, such that the fully convolutional network model outputs a feature image, and the processor generates the path information according to the feature image, wherein the second environment information image, the second direction information image, and the second depth information image are respectively a part of the first environment information image, a part of the first direction information image, and a part of the first depth information image.

15. The surgical robotic arm control method as described in claim 14, wherein before the processor inputs the second environment information image, the second direction information image, and the second depth information image to the fully convolutional network model, the processor first performs image enlargement on each of the second environment information image, the second direction information image, and the second depth information image.

16. The surgical robotic arm control method as described in claim 14, wherein the first depth information image comprises a plurality of first depth planar images corresponding to different depths, and generating the second depth information image comprises:

by the processor, converting the first depth planar images into a plurality of binarized images, and obtaining a plurality of second depth planar images corresponding to different depths in the second depth information image from the binarized images according to the robotic arm distal end region of the surgical robotic arm.

17. The surgical robotic arm control method as described in claim 14, further comprising:

determining, by the processor, that a robotic arm distal end of the surgical robotic arm reaches the target coordinate when the processor determines that the robotic arm distal end region of the surgical robotic arm overlaps the target region.

18. The surgical robotic arm control method as described in claim 17, further comprising:

successively obtaining a plurality of first images by the image capturing unit, such that the processor iteratively executes the spatial environment recognition module, the spatial environment image processing module, and the robotic arm motion feedback module according to the first images to operate the surgical robotic arm a plurality of times to move until the processor determines that the robotic arm distal end of the surgical robotic arm reaches the target coordinate.

19. The surgical robotic arm control method as described in claim 14, wherein a color changing direction of the second direction information image is parallel to a direction from a robotic arm distal end coordinate to the target coordinate in the second direction information image.

20. The surgical robotic arm control method as described in claim 13, further comprising:

providing a target selection signal by an input unit to the processor, such that the processor generates the target coordinate according to the target selection signal.

\* \* \* \* \*